United States Patent [19]

Mintz

[11] Patent Number: 4,643,189
[45] Date of Patent: Feb. 17, 1987

[54] APPARATUS FOR IMPLEMENTING A STANDARDIZED SKIN INCISION

[75] Inventor: Michael Mintz, Edison, N.J.
[73] Assignee: W. T. Associates, Somerville, N.J.
[21] Appl. No.: 703,199
[22] Filed: Feb. 19, 1985
[51] Int. Cl.$^4$ ............................................. A61B 17/32
[52] U.S. Cl. .................................................... 128/314
[58] Field of Search ........................ 128/314, 315, 305

[56] References Cited

U.S. PATENT DOCUMENTS

| | | | |
|---|---|---|---|
| 2,823,677 | 2/1958 | Hein, Jr. ............................... | 128/314 |
| 3,760,809 | 9/1973 | Campbell, Jr. ........................ | 128/314 |
| 4,064,871 | 12/1977 | Reno .................................... | 128/314 |
| 4,157,086 | 6/1979 | Maiorano et al. ................... | 128/314 |
| 4,438,770 | 3/1984 | Unger et al. ......................... | 128/305 |

Primary Examiner—Gene Mancene
Assistant Examiner—C. W. Shedd
Attorney, Agent, or Firm—Arthur L. Plevy

[57] ABSTRACT

There is disclosed apparatus for implementing a standardized skin incision which apparatus includes a housing having a base containing an elongated slot. The base is adapted to be held flush against a patient's skin prior to making an incision. The housing has an internal hollow which contains a movable pivot arm having a first pivotal end and a second end having a cam follower. Located within the housing is a cam surface upon which the cam follower of the pivot arm rides. The pivot end of the arm contains a cutting edge and is coupled to the housing such that it is enabled to move transversely while pivoting. The cam which has a given surface configuration controls the path of the pivot arm and therefore controls the path of the cutting edge as it enters the slot when triggered. The device produces a standard incision of a given length and a given depth as controlled by the reciprocating pivot arm and the cam surface. The device is completely disposable and further possesses the advantage that the cutting edge is always located within the housing except when the unit is triggered where the edge transverses and projects through the slot in the housing for an extremely short period of time. The unit can be fabricated from molded plastic and simple metal parts and is ordinarily sterilized prior to use. Its economy of materials and assembly permit marketing as a completely disposable device.

27 Claims, 20 Drawing Figures

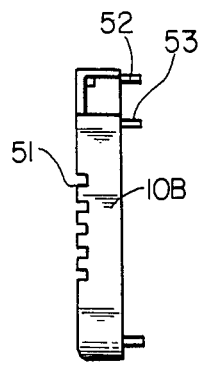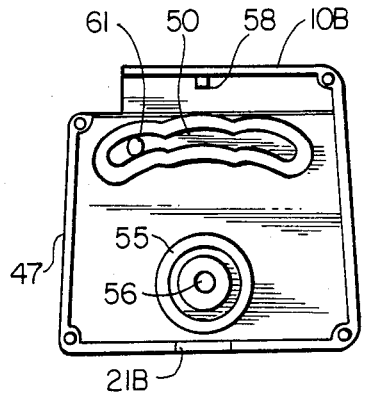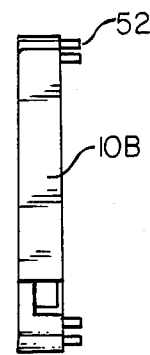
FIG. 5B  FIG. 5A  FIG. 5C
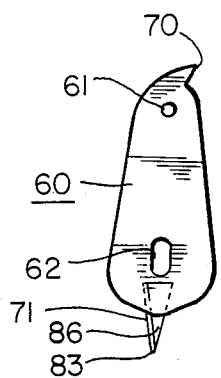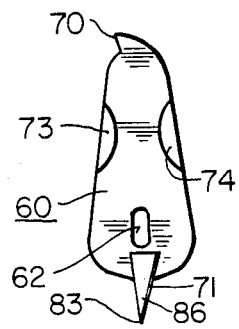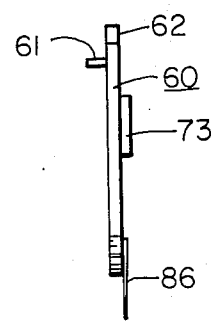
FIG. 6A  FIG. 6B  FIG. 6C
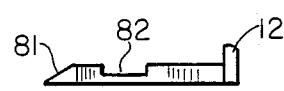
FIG. 7A
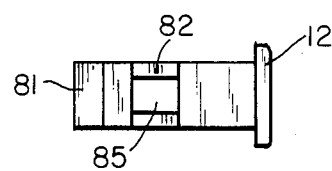
FIG. 7B
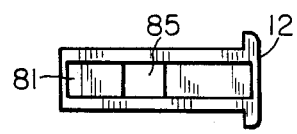
FIG. 7C

APPARATUS FOR IMPLEMENTING A STANDARDIZED SKIN INCISION

BACKGROUND OF THE INVENTION

The present invention relates to apparatus for providing a skin incision in order to cause bleeding and more particularly to a disposable device which provides a precisely controlled incision in the skin of the patient.

Devices for producing skin incisions in the skin of a patient are known in the art and essentially are utilized to permit observation of the bleeding time. The bleeding time is defined as the time between implementing the incision and the moment when the bleeding stops. This is a well known test to determine the ability of blood platelets to stop bleeding from injured vessels. Many techniques have been described in the literature as well as in certain prior art devices. Essentially, bleeding tests were first performed by surgeons or technicians who employed a scalpel to make an incision which was a relatively small incision at a relatively small depth. Such wounds as implemented by scalpels or lancets produced incisions which were 5 to 10 mm long and 1 to 5 or more mm deep. The need for disposable devices to automatically produce such incisions was apparent due to the fact that many persons have fear of a scalpel as well as the further fact that the length and depth of the incision was a pure function of the ability of the practitioner and hence such incisions could vary widely depending upon the skills of the practitioner.

To circumvent such problems, a series of devices are described which essentially seek to provide a standardized skin incision in order to cause bleeding so as to make it proper to determine bleeding time as above indicated. U.S. Pat. No. 3,902,475 which issued on Sept. 2, 1975 entitled DEVICE FOR MAKING SKIN INCISIONS by Geoffrey Berg et al shows a device for forming a skin incision which device has a base plate having a lower surface which is adapted to be placed against the skin of a patient. The base plate has an elongated aperture. Extending from the base plate is a support member having a cutting edge which is aligned with the aperture. The device includes a fixed pivot for mounting said support member and cutting edge for pivotal rotation about an axis parallel to the slot.

Upon actuation of the instrument, the cutting edge moves through an arc of a circle from points above the lower surface of the base plate and then enters the slot where the cutting edge projects into the patient's skin during the arcuate path and makes an incision over a given length. This device, while eliminating the above noted problems of manual incisions, has many disadvantages. First the device produces an incision which is not of a uniform depth based on the fact that the cutting edge traverses an arc. Hence the incision made is longer than necessary in order to obtain at least a length of 5 mm at a depth of at least one or more mms to assure bleeding. Due to the pendulum-like path, the incision is arcuate and is not of a constant depth. Hence most of the cut made by this instrument does not produce bleeding. Although the instrument is simple in structure it has the above noted disadvantages.

U.S. Pat. No. 4,078,552 entitled DEVICE FOR AND METHOD OF MAKING STANDARD AND REPRODUCEABLE SKIN PUNCTURES issued on Mar. 14, 1978 to Evan N. Chen et al and assigned to the Warner-Lambert Company. This device is commercially sold under the trade name SIMPLATE. Essentially, as is disclosed in the patent, the device contains a blade or cutting edge which is located in a housing and which housing contains a blade aperture. The blade is supported by a post which post has a spring surrounding the same. When a release mechanism associated with the housing is activated, the spring pushes the blade downwardly much like the action of a guillotine, and hence the blade penetrates the patient's skin in a downward thrust as in the vertical direction making a standard puncture which puncture is approximately 5 mm in lenth and 1 mm in depth. This device, while having gained wide spread acceptance has many problems associated therewith.

First, the blade once activated to penetrate the patient's skin cannot be retracted and is exposed and is dangerous to both the technician and the patient. A further problem with the instrument is that the blade has to remain within the patient's skin for at least one second after it has been activated. This is due to the fact that a puncture which is made by a vertical thrust is not analogous to the type of incision made by a scalpel or to the incision made by the above noted device. Essentially, it is not a cut formed by moving a scalpel or blade along the skin but is a wound which is made by a downward thrust of a blade into the skin.

Both of the above noted patents contain various details concerning the need for bleeding time tests and include various explanations which are pertinent to the general problems.

It is, therefore, a major object of the present invention to produce apparatus for implementing a standardized skin incision which apparatus is disposable and which circumvents the above noted problems inherent in prior art devices.

The apparatus to be described produces a surgical cut which simulates the cut of a surgeons scalpel as opposed to an arcuate cut or puncture and produces the cut at the proper length and depth to assure accurate bleeding time measurements as required. A further advantage of the apparatus is that it is extremely simple to implement and manufacture. A further advantage of the apparatus to be described is that based on its operation, the cutting blade spends very little time in implementing the incision since the action is extremely rapid as compared to the apparatus for example shown in U.S. Pat. No. 4,078,552.

BRIEF DESCRIPTION OF THE PREFERRED EMBODIMENT

Apparatus for implementing a standardized skin incision, comprising a housing having an internal hollow and having located on a surface an elongated slot, with said slotted surface adapted to be placed flush against the skin, a cam surface located on one side of said housing within said hollow, a pivot arm having a first pivotable end and a second end having means adapted to engage with said cam surface, with said pivotable end coupled to a surface of said housing to allow said arm to pivot at a location apart from said cam surface, means associated with said arm to allow said arm to move in a transverse direction to said slot while pivoting, said arm further including a cutting edge coupled thereto which cutting edge extends through said slot when said arm is pivoted and spring biasing means coupled to said arm to bias said arm in a first position where said cutting edge is within said housing and an activatable trigger means coupled to said arm to hold said arm in said first postion and to release said arm when activated to cause said edge to traverse through and along said slot in a path according to said cam surface to provide an incision in the skin of a length relatively equal to the length of said slot and substantially of a uniform depth.

BRIEF DESCRIPTION OF THE DRAWINGS

FIG. 5A is an inside view depicting the other housing section associated with the apparatus.

FIG. 5B is an end view of FIG. 5A.

FIG. 5C is a top view of FIG. 5A.

FIG. 6A is a front view of a pivot arm and a cutting edge employed in this invention.

FIG. 6B is a rear view of FIG. 6A.

FIG. 6C is a side view of FIG. 6A.

FIG. 7A is a side plan view of a plunger or trigger mechanism employed in this invention.

FIG. 7B is a top view of FIG. 7A.

FIG. 7C is a bottom view of FIG. 7A.

DETAILED DESCRIPTION OF THE DRAWINGS

Figure 1:
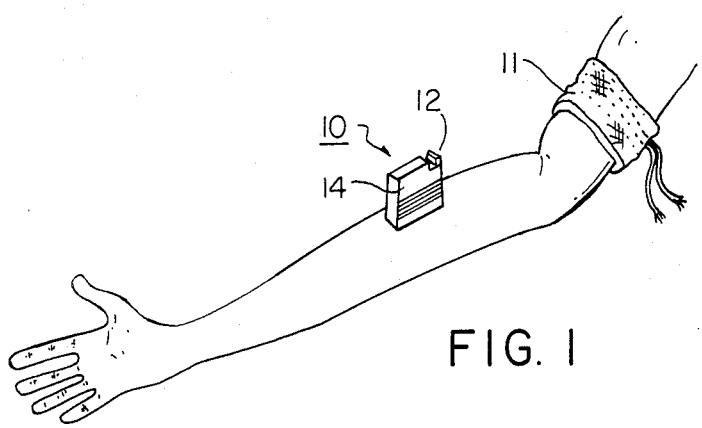
FIG. 1 is a perspective plan view depicting a patient's arm for describing operation of the apparatus according to this invention.

Referring to FIG. 1, there is shown a device 10 for performing a skin incision according to this invention.

Essentially, as seen in FIG. 1, before an incision is made, a pressure sleeve or sphygmomanometer cuff 11 is emplaced about the patient's upper arm. The cuff is then inflated to a pressure of about 40 mm of mercury. The device 10 is placed on the patient's forearm where the incision may be made either parallel or perpendicular to the fold of the patient's elbow. The device 10 contains a trigger mechanism or trigger plunger 12 which plunger is pressed inwardly to release the cutting edge as will be explained. Essentially, the cutting edge is completely within the housing 14 of the device 10 and is not exposed in any manner whatever until the trigger mechanism 12 is activated. When the trigger mechanism 12 is activated, a cutting edge traverses a slot in the base of the housing which is flush against the patient's skin and makes an incision of a given length and of a uniform depth as above described.

The device is relatively small and, as indicated, is disposable as being entirely fabricated from conventional plastic and metal materials.

Figure 2:
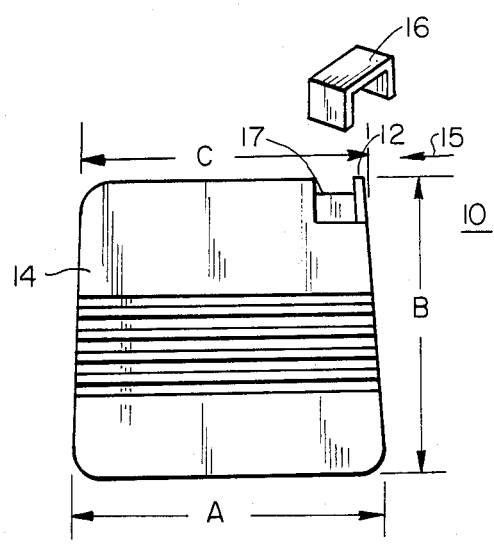
FIG. 2 is a side view of the skin incision apparatus according to this invention.

Referring to FIG. 2, there is shown a side view of the device 10. Essentially, as will be explained, the housing 14 is comprised of first and second sections which are secured together by conventional means. The trigger mechanism 12 is shown. To activate the device, the trigger mechanism 12 is pushed inwardly to release a pivot arm as will be explained. The trigger mechanism 12 is a plunger device which essentially is supported by a rail in the housing to enable it to move in the direction of arrow 15. Thus to activate the device, the technician or practitioner must push the member 12 inwardly. In order to prevent inadvertent operation, a keeper or safety device 16 is shown. The device 16 is a U-shaped member which essentially is positioned in the space 17 of the housing and prevents the plunger 12 from being moved when the device 16 is emplaced on the housing.

In order to gain some insight of the dimensions of an actual unit, a typical unit has a height B of approximately 1⅛" with a bottom width A of 1⅜", with a top length C (FIG. 4A) of about 1 1/16" and with a width D (FIG. 3 A) of about 7/16". The dimensions can vary of course, but as one can ascertain, the unit is relatively small.

Figure 3A:
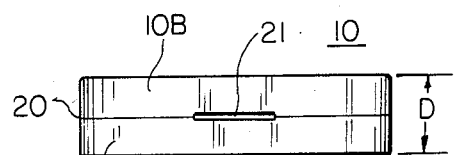
FIG. 3A is a bottom plan view of the apparatus.

Referring to FIG. 3A, there is a bottom view of the unit 10 showing that it is comprised of two housing sections 10A and 10B which sections are secured together at location 20. The bottom or base of the unit 10 has a slot 21 which is elongated and through which slot the cutting edge is directed, as will be explained.

Figure 3B:
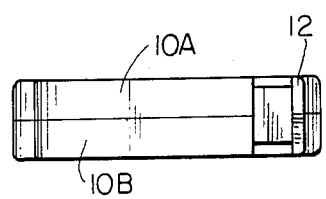
FIG. 3B is a top plan view of the apparatus.

Referring to FIG. 3B, there is shown a top view depicting the plunger mechanism 12 together with the housing sections 10A and 10B.

Figures 4A, 4B:
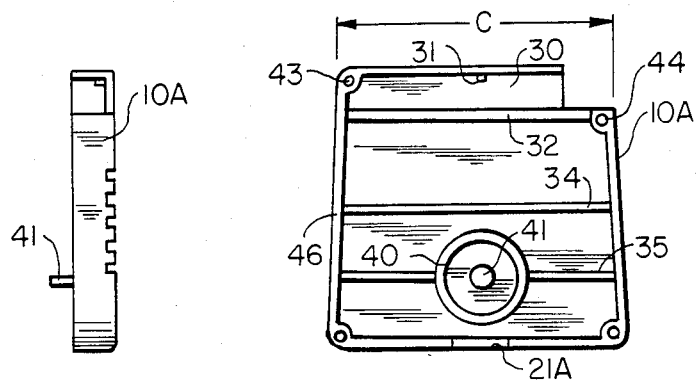
FIG. 4A is a an inside view of a first housing section of the apparatus.
FIG. 4B is a an end view of FIG. 4A.

Referring to FIG. 4A, there is shown an internal plan view of the first housing section 10A. Essentially, as can be seen from FIG. 2, the housing section 10A is molded from a suitable plastic and has a top channel 30 which accommodates the plunger member 12. The channel has a projecting boss 31 located on the top surface which boss holds the plunger before activation of the unit. A rail 32 is shown in the housing to guide the plunger so that it travels in the direction of arrow 15. The housing section 10A contains supporting ribs as 34 and 35 to provide a guide for travel of a pivot arm, as will be explained. Located near the bottom portion of the housing is a circular boss 40 which surrounds an extending rod 41. The rod 41, as will be explained, acts as a pivot point for the pivot arm which arm contains the cutting edge. Also shown in FIG. 4A is half a slot 21 designated as 21A.

FIG. 4B depicts an end view of the housing section 10A showing the rod 41 extending therefrom.

Figure 4C:
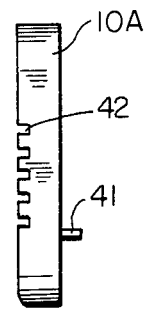
FIG. 4C is an opposite end view of FIG. 4A.

FIG. 4C depicts an opposite end view of the housing section 10A showing the rod 41 as extending from the circular boss 40. It is noted that the outer surface of the housing section 10A has a series of grooves 42 which provide an aesthetic appearance to the unit as well as for user grip, strength and rigidity. Housing section 10A also contains a series of apertures as 43 and 44 and so on. These apertures accommodate extending rods associated with the other housing section 10B to allow the two units to be coupled together and essentially are formed along the outer peripheral flange 46 of the section 10A.

Referring to FIG. 5A, there is shown an internal view of section 10B. Section 10B also has an outer peripheral flange 47 and contains on an inner wall a convoluted cam channel 50. The channel 50, as will be explained, accommodates a cam follower or rod associated with the pivot arm to allow the pivot arm to move strictly according to the convolutions formed in the upper and lower surfaces of the cam channel 50. Also shown in FIG. 5A is the other half of slot 21 designated at 21B. Thus as one can ascertain, when housing sections 10A and 10B are placed together or in congruency, the slot 21 is formed by partial slots 21A and 21B.

FIG. 5B depicts an end view of housing section 10B which also has grooves 51 on the outer surface and has projecting pins as 52 and 53 which coact with the apertures as 43 and 44 in housing section 10A.

FIG. 5C shows a top view of housing section 10B showing the projecting rods as 52 which coact with the apertures in the flange of housing section 10A. Also shown in FIG. 5A is a projecting circular boss 55 which contains a central aperture 56 to accommodate the extending rod 41 when the housing sections are placed together during assembly. Thus as one can ascertain, the rod 41 extends into aperture 56 and forms a pivot bar for the pivot arm to be described.

Referring to FIG. 6A, there is shown a top view of a pivot arm 60. The pivot arm 60 has an extending cam follower rod 61 which rod extends into the convoluted cam channel 50 as shown in FIG. 5A. The convoluted cam surface of the cam channel 50 as will be explained controls the movement of the pivot arm and, therefore, of the cutting edge 71 of blade 83 when the unit is activated.

Also shown in FIG. 6A there is an elongated aperture 62 associated with pivot arm 60. This aperture 62 is emplaced over the extending rod 41 and, as can be seen, allows the pivot arm 60 to move in transverse directions and at distances determined by the convoluted cam surface. Located on the top of the pivot arm is a keeper section 70 which, as will be explained, coacts with the end of the plunger arm to retain the pivot arm in a first position prior to device actuation. Coupled to the pivot arm 60 is a triangular blade 86 with cutting edge 71 and sharpened apex 83. The blade 86 may be secured to the pivot arm by any conventional means and is scalpel-like in appearance and function. As shown, the blade 86 is of triangular configuration having a sharpened apex 83 which will produce the required incision.

Referring to FIG. 6B, there is shown a bottom view of the pivot arm 60. The bottom side contains two projecting arcuate areas 73 and 74 which, as will be explained, are employed to accommodate a spring.

Referring to FIG. 7A, there is shown a side view of the plunger mechanism 12. The plunger 12 has a sloping front end 81 which front end coacts with section 70 of the pivot arm 60 during operation, as will be explained. The plunger also contains a top channel 82 which channel abuts against the stop members as 31 of section 10A and 58 of section 10B to hold the pivot arm secure in position when the front surface 81 coacts with the upper section 70 of the pivot arm 60.

FIG. 7B shows a top view of the plunger member 12 utilizing the same reference numerals.

FIG. 7C shows a bottom view of the plunger member 12. There is a rectangular aperture 85 in the plunger member to allow the same to coact with the stop members 31 and 58.

Figure 8:
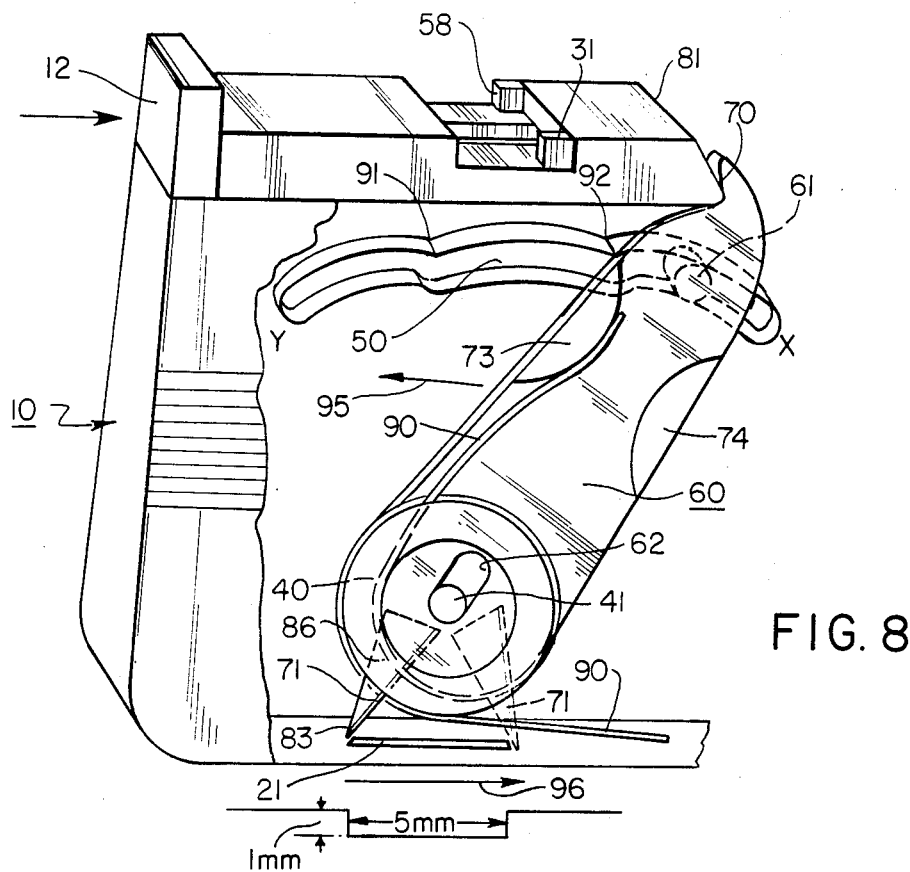
FIG. 8 is a partial assembly view of the skin incision apparatus according to this invention and necessary to explain the operation of the mechanism.

Referring to FIG. 8, there is shown a partial assembly view of the components described above. FIG. 8 uses the same reference numerals as utilized in the above figures for the sake of clarity and to show operation.

Essentially, when the housing sections 10A and 10B are placed together with the pivot arm 60 having its aperture 62 inserted about rod 41, the blade 86 containing cutting edge 71 is positioned above the slot 21 but is located within the housing 10 in the non-active position as shown in FIG. 8. The means for biasing the pivot arm constitutes a coiled wire spring 90. The spring 90 is directed about the circular boss as 40 and extends to the pivot arm where it is retained at one end by the arcuate projection 73. The other end of the spring 90 is positioned against the bottom wall of the housing 10. The cam follower rod 61 is positioned within the cam channel 50 located on the inner wall of the housing section 10B. The plunger arm 12 has its front surface 81 coacting with the keeper section 70 of the pivot arm and is held in position by means of projections as 31 and 58 abutting against the wall of top channel 82 of the arm 12. Thus as can be seen from FIG. 8, the pivot arm, when in the position shown, is biased by means of the spring 90 which compresses based on its loop structure to store spring energy. The pivot arm 60 is kept in that position by means of plunger 12 which restrains the pivot arm from moving.

As the plunger arm is pushed inwardly, the sloping surface 81 pushes the pivot arm towards the right until the pivot arm clears the sloping front wall of the plunger 12. At this position, the spring 90 pivots the entire arm 60 in the direction of arrow 95 thus causing the cutting edge to move in the direction indicated by arrow 96 or from left to right through the slot 21. The pivot arm is constrained to move by means of the cam surface 50 which surface converts the normal arcuate movement of the arm into a segmented linear movement as shown in the diagram beneath FIG. 8. Hence the convoluted cam surface together with the aperture 62 causes the cutting edge to actually reciprocate so that the cutting edge 71 traverses the patient's skin always at a relatively given depth of 1 mm and a length of 5 mm which is determined by the shape and end limits imposed by the intermediate cam convolutions 91 and 92 of the cam channel member 50. Thus as one can see, the normal arcuate motion of the pivot arm is converted so that the incision made by the cutting edge 71 entering the slot 21 is of relatively uniform depth and length. The arm 60 will pivot from side X of channel 50 to side Y of channel 50. The cutting blade 86 will, therefore, move from side Y to side X and will be directed below the slot to penetrate the patient's skin. The operation is such that apex 83 punctures the skin and thereafter cutting edge 71 incises the skin. At the end of travel, the blade 86 including apex 83 is withdrawn from the skin back into the housing.

Figure 9:
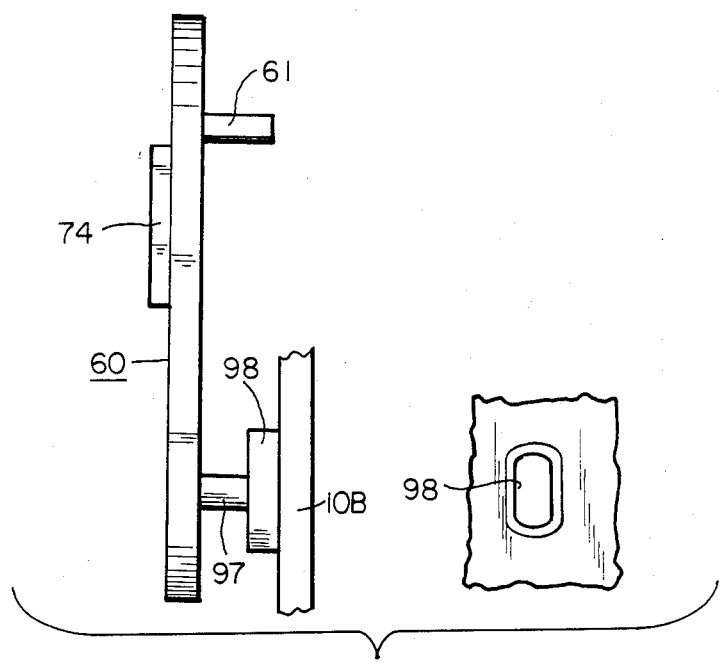
FIG. 9 is a partial view depicting an alternate embodiment for a movable pivot mechanism used in this invention.

As shown in FIG. 9, alternatively, the pivot arm 60 having the cam follower section 61 may contain a separate pivot rod 97 which rod is to be inserted into a channel 98 located on the corresponding side wall as the side wall of section 10B. In this manner, the pivot arm can also move in directions transverse to the slot 21 based on the path determined by the convoluted cam surface. Thus from the above description it is seen that the apparatus according to this invention allows the pivot arm which contains the cutting edge to move along and transverse to the slot under the influence of the cam surface and hence one provides an incision of a given length and of a uniform depth which incision actually simulates the type of incision which would be implemented by a surgeons's scalpel.

Figure 10:
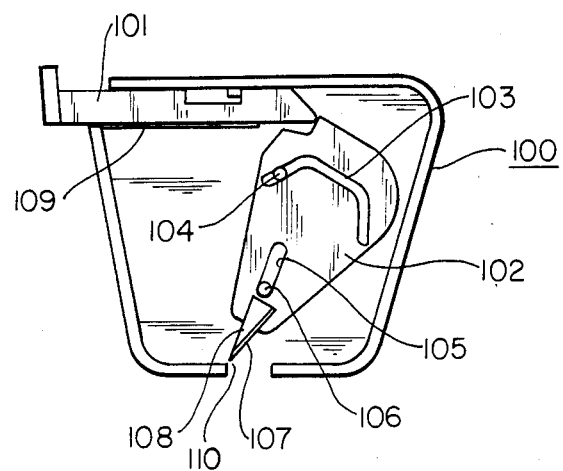
FIG. 10 is an alternate embodiment of a skin incision apparatus according to this invention.

Referring to FIG. 10, there is shown a front view of an alternate embodiment of the cutting mechanism. The housing 100 is of a tapered configuration to show that the housing 10 of FIG. 1 may be of any convenient shape. The mechanism depicted in FIG. 10 operates on similar principals to that previously described. As seen from FIG. 10, the pivotable member 102 has an arcuate cam slot 103 in substantially the shape of the cross section of an inverted trough located on the surface. A rod 104 which is secured to the housing acts as a cam follower. The pivot member 102 has an elongated aperture 105 into which is inserted a rod 106 also secured to the housing. The rod 106 allows the arm 102 to move transversely. Secured to the arm 102 is a blade 108 having a cutting edge 107 and an apex 110.

The trigger mechanism 101 or plunger acts in the same manner as plunger 12 depicted above. The pivot arm 102 coacts with a coil spring which may be directed about the annular members as spring 90 of FIG. 8. As one can see from the above description, the arm 102 will move as controlled by the cam slot 103 to produce the required cut as explained previously in conjunction with FIG. 8. Therefore, as one can ascertain from FIG. 10, the major difference of the apparatus shown in FIG. 10 is that the pivot arm 102 contains the cam surface 103 in the form of a slot, while the cam follower 104 is rigidly secured to the housing as shown.

Figure 11:
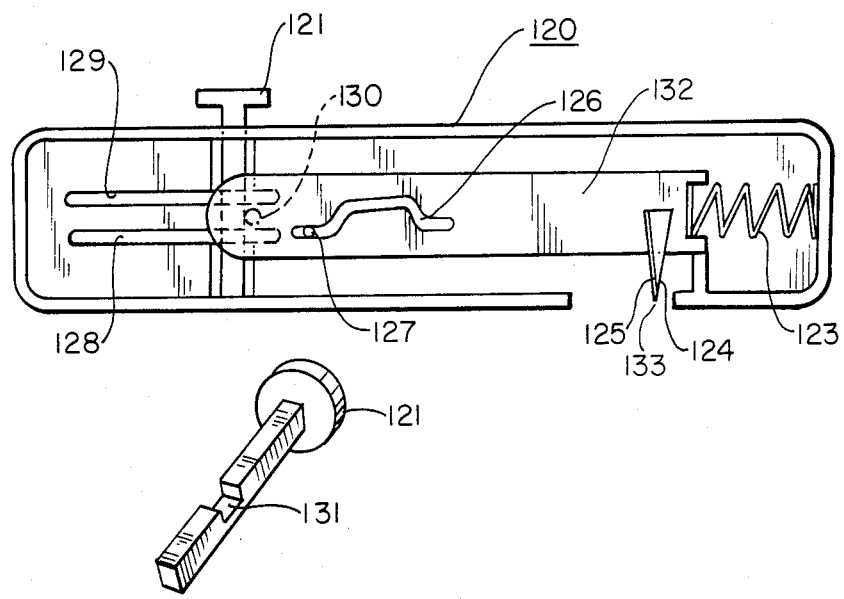
FIG. 11 depicts another embodiment according to this invention.

Referring to FIG. 11, there is shown a further alternate embodiment of a device for making an incision. Essentially, there is shown a housing 120 which is elongated in shape and having an internal hollow cavity. Located within the housing 120 is an elongated movable member 132. The member 132 is coupled at one end to the wall of the housing via a coiled spring 123. In the position shown, the member 132 compresses the spring 123. The member 132 is held in position by means of a trigger plunger mechanism 121 which as will be explained when actuated releases member 132.

Coupled to member 132 is a cutting blade 124 having a cutting edge 125 with an apex 133 as the blades described above. The member 132 has a cam slot 126 in substantially the shape of the cross section of an inverted trough which cam slot 126 coacts with a cam follower rod 127 which is secured to the inner wall of housing 120. Located on the other side of the member 132 is a projecting rod 130. The rod 130 rides between two elongated projections as 128 and 129 also secured to inner wall of housing 120. The projections 128 and 129 are spaced apart to allow the rod 130 and member 132 to translate and pivot between the projections 128 and 129 according to the control path dictated by the cam slot 126 and the follower 127. The trigger mechanism 121 as shown below in perspective plan view has an aperture 131. The aperture 131 allows the rod 130 to be released when the member 121 is pushed inwardly. This causes the cutting blade 124 to transverse the slot according to the shape of the cam aperture 126. In this manner the cutting edge as propelled by the spring will first puncture the skin of the patient and then travel in a straight line and then retract from the skin with the edge in the final position being maintained within the confines of the housing as described above in the other embodiments. Thus as one can ascertain, the embodiments depicted in FIGS. 8, 10 and 11 all provide the same type of controlled path for the cutting edge. In this manner each of the embodiments contains a pivotal member which member can move parallel to the opening as well as transverse to the opening as controlled by a cam surface which surface may be located on the housing or on the movable member.

The exact dimensions of the incision as to depth and length can be accurately controlled while the blade is within the housing before activation and only projects from the housing when an incision is being made. After the incision is made, the blade again is returned to the hollow confines of the associated housing.

The operation of the device is extremely rapid as determined by the spring factor. Thus the cutting edge traverses the slot in an extremely short period which is on the order of many milliseconds or much less than a second.

The patient hardly feels the incision as it is done rapidly and reliably. Furthermore, the incision as indicated is of a uniform depth and length, and hence there is no unnecessary cutting in order to produce reliable bleeding while the blade or cutting edge, reenters the housing and is not exposed after the unit has been activated.

Thus apart from resolving all of the above mentioned problems associated with prior art devices, the unit has the further advantages that it is extremely inexpensive to fabricate as all parts are made from molded plastic with the exception of the blade and the coiled spring.

While the above description and dimensions are given by way of example, it will become apparent that there are many alternative techniques which can be employed in modifying the invention as above described. All such techniques shall be deemed to be encompassed within the breadth and scope of the claims appended herewith.

I claim:

1. Apparatus for implementing a standardized skin incision, comprising:

a housing having an internal hollow and having located on a surface an elongated slot, with said slotted surface adapted to be placed flush against the skin, an arcuate cam surface having a series of convolutions located within said hollow, a movable arm having a first pivotal end and a second end having means adapted to engage with the cam surface, with said pivotable and end coupled to a surface of said housing to allow said arm to pivot at a location apart from said cam surface, means associated with said arm to allow said arm to move in a transverse direction to said slot while pivoting along said slot, said arm further including a cutting edge coupled thereto which cutting edge extends through said slot when said arm is pivoted, and spring biasing means coupled to said arm to bias said arm in a first position where said cutting edge is within said housing and an activatable trigger means coupled to said arm to hold said arm in said first position and to release said arm when activated to cause said edge to traverse through and along said slot in a path according to said cam surface to provide an incision in the skin of a given length and substantially of a uniform depth.

2. The apparatus according to claim 1, additionally comprising an extending rod coupled to said housing surface, and said pivotable end of said arm having an elongated aperture for positioning about an extending rod coupled to said housing surface to allow said arm to move in said transverse direction to follow said convolutions when pivotally moving along said slot.

3. The apparatus according to claim 1, wherein said housing surface includes an elongated aperture, and said pivotable arm has an extended pivot rod at said pivotable end, for engaging said elongated aperture for accommodating said rod to allow said arm to move in said transverse direction to follow said convolutions when pivotally moving along said slot.

4. The apparatus according to claim 1, wherein said spring bias means is a spring wire having one end secured to said arm and directed about the pivot point end and said other end secured to said housing to enable said spring wire as directed about said pivot point end to store energy in said first position.

5. The apparatus according to claim 1, wherein said trigger means comprises a movable member having a first end located outside said housing and a second end in contact with said arm to hold the same in said first position, said trigger means when moved adapted to release said arm to allow said arm to move under the influence of said spring bias means.

6. The apparatus according to claim 1, wherein said means on said arm adapted to engage with said arcuate cam surface comprises an extending rod coacting with said arcuate cam surface whereby said rod follows said surface as said arm is pivoted.

7. The apparatus according to claim 1, wherein said cam surface is configured to cause an incision approximately 5 mm long by 1 mm in depth.

8. The apparatus according to claim 1, wherein said housing is generally rectangular in shape with said bottom surface having said elongated slot adapted to be placed flush against the skin.

9. Apparatus for implementing a standardized skin incision comprising:
a housing having an internal hollow and having located on a surface an elongated slot with said surface configured to be placed flush against the skin of a patient,
cam means coupled within the hollow of said housing and having a given arcuate surface having a series of convolutions and directed above said housing surface and positioned above said slot,
a movable arm pivotally secured to said housing on a surface within said hollow and having a pivot point on a surface and having a cam coacting means whereby said arm can pivot along a path traversing said slot, and means coupled to said arm to allow said arm to also move transverse to said slot while pivoting along said slot, cutting edge means coupled to said arm and positioned within said housing in a first position of said arm and adapted to extend through said slot when said arm is moving,
spring bias means coupled to said arm to exert a spring force on said arm in said first position, activatable releasing means coupled to said housing and coacting with said arm when activated whereby said arm due to said spring energy traverses said slot causing said cutting edge means to enter said slot and perform an incision according to the movement of said arm as controlled by said cam surface.

10. The apparatus according to claim 9, wherein said means coupled to said arm to allow said arm to move in a transverse direction includes an elongated aperture in said arm and a rod extending from a housing wall and directed through said aperture to serve as a pivot point with said aperture allowing said arm to move transverse to said slot as riding along said rod and according to the convolutions on said arcuate cam surface.

11. The apparatus according to claim 9, wherein said means coupled to said arm to allow said arm to move in a transverse direction includes an extending rod located on said arm defining a pivot point, with an internal surface of said housing having a transverse slot into which said rod is inserted to allow said arm to move in said transverse direction according to said convolutions on said arcuate cam surface.

12. The apparatus according to claim 9, wherein said cam coacting means comprises an extending projection located on said arm at said other end for coacting with said cam surface.

13. The apparatus according to claim 9, wherein said housing is generally rectangular in configuration with said bottom surface having said elongated slot adapted to be placed flush against the skin.

14. The apparatus according to claim 9, wherein said spring bias means is a wire spring having one end coupled to said arm and looped about the pivot end of said arm with the other end coupled to said housing whereby when said arm is placed in said first position said loop portion compresses to exert said spring force.

15. The apparatus according to claim 9, wherein said activatable releasing means includes an elongated plunger member having first and second ends, said housing having an aperture in a sidewall for accommodating said member with one end extending through said aperture outside said housing and said other end contacting said arm in said first postion to hold said arm whereby when said plunger member is moved with respect to said housing said arm is released to pivot.

16. The apparatus according to claim 15, further including removable safety means coupled to said plunger to prevent movement of said plunger when said plunger holds said arm in said first position and when removed allows said plunger to be manually moved.

17. The apparatus according to claim 9, wherein said cam surface is configured to cause an incision approximately 5 mm long and 1 mm in depth.

18. The apparatus according to claim 9, wherein said housing is fabricated as first and a second sections which are secured together to form said housing with said internal hollow.

19. The apparatus according to claim 9, wherein said cutting edge means is a blade of a triangular configuration with an apex of said triangle being directed towards said elongated slot to provide said incision.

20. An improved device for forming a skin incision, said device of the type including a cutting edge which is caused to traverse a path upon the pivotal movement of an arm member coupled to said cutting edge, the improvement for causing said edge to traverse a relatively linear path when said member is pivoted, comprising in combination:
a single cam member including a single slotted cam surface taking the form of a cross section of an inverted trough, said cam surface including first and second slotted sides of opposite slope and of equal length forming sides of said trough, said first and second slotted sides converging in a direction away from said edge, a central slotted straight line portion joining opposing ends of said first and second sides to define a closed portion of said trough to compensate for an arcuate path movement, and cam follower means coupled to said arm member to control movement of said arm and means coupled to said arm to allow said arm to move in directions transverse to said arcuate path while pivoting to thereby cause said cutting edge to provide an incision in the skin of a patient of a given length and substantially of a predetermined depth along said given length with the first side of said cam surface constraining said cutting edge to move in a direction to penetrate said patient's skin at a given depth and to travel a given distance at said depth due to said central portion and then to withdraw as constrained by said second side.

21. An apparatus for implementing a standardized skin incision comprising:
a housing having an internal hollow and having located on a surface an opening, with said surface adapted to be placed flush against a patient's skin,
a movable member within said hollow,
a blade coupled to said movable member having a cutting edge and a sharpened apex,
a single cam including a single slotted cam surface taking the form of a cross-section of an inverted trough, said slotted cam surface having first and second sides of equal length and opposite slope forming sides of said trough, said first and second sides diverging with respect to said opening and converging toward a closed portion of said trough, a central slotted atraight line portion joining opposing ends of said first and second sides to define said closed portion of said trough to define a controlled path including cam follower means associated with said housing and said movable member to allow said movable member to move within constraints imposed by said cam and follower means and causing said apex of said blade to trace a controlled path through said opening with the first side of said cam surface constraining said blade to move through said opening and out of said hollow to penetrate said patient's skin at a given depth and to travel a given distance at said depth due to said central portion and then to withdraw back into said hollow constrained by said second side to cause said cutting edge to incise said patient's skin,
activatable trigger means coupled to said movable member to hold said movable member in a first position where said cutting edge and sharpened apex are within said housing and to release said movable member to cause said apex to traverse said controlled path when activated,
biasing means coupled to said movable member to bias said movable member in said first position and to provide a motivating force to move said movable member when said trigger means is activated.

22. The apparatus according to claim 21, wherein said controlled path comprises essentially three-segments, a first segment comprising essentially a line, normal to said housing surface and extending from said apex in said first position to a second position below the surface of said patient's skin a second segment comprising essentially a line, parallel to said housing surface and extending from said second position to a third position below the surface of said patient's skin, a third segment comprising essentially a line, normal to said housing surface and extending from said third position to a final position within said housing.

23. The apparatus according to claim 21, wherein said opening is a slit through which said blade may pass without interference when said apex traces said path.

24. The apparatus according to claim 21, wherein there is provided pivot means associated with a wall of said internal hollow and said movable member whereby said movable member may move with both translational and rotational motion.

25. The apparatus according to claim 21, wherein said movable member is a pivot arm member having a pivotable end including means for allowing said arm to reciprocate transversely with respect to said opening and having a cam follower at said other end for coacting with said cam.

26. The apparatus according to claim 21, wherein said movable member includes said cam means comprising a slot in said movable member of a configuration for defining said controlled path and follower means coupled to said housing to cause said movable member to follow said controlled path when moving.

27. The apparatus according to claim 21, wherein said movable member comprises an elongated bar having said cutting edge coupled to one end with said bar adapted to move parallel to said slot, and having located on said bar a cam surface aperture to allow said bar when moving to pivot transversely to said opening, with follower means coupled to said housing and coacting with said cam surface aperture to thereby cause said bar to follow said controlled path.

* * * * *